US00PP35194P3

(12) United States Plant Patent
Olesen

(10) Patent No.: US PP35,194 P3
(45) Date of Patent: May 30, 2023

(54) ROSE PLANT NAMED 'POULPAH110'

(50) Latin Name: *Rosa hybrida*
Varietal Denomination: Poulpah110

(71) Applicant: Mogens Nyegaard Olesen, Fredensborg (DK)

(72) Inventor: Mogens Nyegaard Olesen, Fredensborg (DK)

(73) Assignee: Poulsen Roser Als, Fredensborg (DK)

( * ) Notice: Subject to any disclaimer, the term of this patent is extended or adjusted under 35 U.S.C. 154(b) by 0 days.

(21) Appl. No.: 17/803,632

(22) Filed: Sep. 13, 2022

(65) Prior Publication Data

US 2023/0103293 P1 Mar. 30, 2023

(30) Foreign Application Priority Data

Sep. 24, 2021 (QZ) ..... PBR 2021/2364

(51) Int. Cl.
*A01H 5/02* (2018.01)
*A01H 6/74* (2018.01)

(52) U.S. Cl.
USPC ..... Plt./119

(58) Field of Classification Search
USPC ..... Plt./101, 116, 119
See application file for complete search history.

(56) References Cited

PUBLICATIONS

Poulsen Roser website. 2022. citation for Lenora. https://www.poulsenroser.dk/en/Roses/ShowProduct/82408. 1 page. (Year: 2022).*

* cited by examiner

*Primary Examiner* — Karen M Redden

(57) ABSTRACT

A new garden rose plant of the miniature class which has abundant, orange flowers and attractive foliage. This new and distinct variety has shown to be uniform and stable in the resulting generations from asexual propagation.

1 Drawing Sheet

Botanical designation: *Rosa hybrida.*

Variety denomination: 'Poulpah110'.

This application claims priority to Plant Breeder's Rights Application Number 2021/2364, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2016 and the resulting seeds were planted in a controlled environment in Fredensborg, Denmark. The new variety, named 'Poulpah110', originated as a single seedling from the stated cross.

The new variety may be distinguished from its male pollen parent and female seed parent primarily by the following characteristics. The male pollen parent plant has yellow flowers while the new variety has orange flowers. The female seed parent plant has small orange flowers, with a diameter of 55 mm, while the newly claimed plant has larger flowers 80 mm in diameter. The objective of the hybridization of this rose variety was to create a new and distinct variety with unique qualities, such as:

1. Uniform and abundant orange flowers;
2. Vigorous, but compact growth when propagated on its own roots;

3. Suitability for production in six inch containers; and
4. Exceptional disease resistance.

This combination of qualities is not present in previously available commercial cultivars of this type, known to the inventor, and distinguish 'Poulpah110' from all other varieties of which we are aware.

As part of the rose development program, Mogens N. Olesen germinated the seeds from the aforementioned hybridization during winter of 2016 and conducted evaluations on the resulting seedlings in a controlled environment in Fredensborg, Denmark. 'Poulpah110' was selected in the spring of 2017 by the inventor as a single plant from the progeny of the aforementioned hybridization.

Asexual reproduction of 'Poulpah110' by rooted cuttings was first done by Mogens N. Olesen in the nursery in Fredensborg, Denmark in July, 2017. This initial and other subsequent asexual propagations conducted in controlled environments have demonstrated that the characteristics of 'Poulpah110' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah110'. Specifically illustrated in the drawing are open flowers viewed from above, flower bud before opening and while opening, flower petals detached revealing reproductive flower parts, sepals detached, mature and juvenile leaves and bare stem. Plants shown are 2 years of age.

DETAILED DESCRIPTION OF THE VARIETY

The following is a description of 'Poulpah110', as observed in its growth in a glass house located in Odense Denmark. Observed plants are 6 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpah070', U.S. Plant Pat. No. 27,641 are compared to the claimed plant 'Poulpah110'. The general tonality of flower for the claimed plant is Open flowers are Yellow-Orange Group 23B with intonations of Orange-Red Group 31A. As the flower matures color changes to Yellow-Orange Group 18A and other colors of Orange Group 29A. The general tonality of the comparison variety 'Poulpah070' is Yellow-Orange Group 23C with other intonations of Orange Group 25C and Orange-Red Group 32B. The claimed plant has a flower diameter of 80 mm while the comparison variety has a flower diameter of 55 mm.

FLOWER AND FLOWER BUD

Blooming habit: Continuous.

Flower bud:

- *Size*.—Upon opening, 23 mm in length from base of receptacle to end of bud. Bud diameter is 16 mm.
- *Bud form*.—Ovoid.
- *Bud color*.—As sepals divide petals are Greyed-Orange Group 176B, Red Group 47B & Yellow-Green Group 145C.
- *Sepal inner surface*.—Color: Yellow-Green Group 147B. Surface: Lightly pubescent.
- *Sepal outer surface*.—Color: Yellow-Green Group 146A with intonations of Greyed-Purple Group 187B. Texture: Smooth.
- *Sepal shape*.—Apex: Cirrhose. Base: Flat at union with receptacle.
- *Sepal margin*.—Margins have weak foliaceous appendages on three of the five sepals.
- *Sepal size*.—45 mm long, 7 mm wide.
- *Receptacle*.—Texture: Smooth. Size: 15 mm in height, 10 mm wide. Color: Yellow-Green Group 144A. Shape: Funnel, long.
- *Pedicel*.—Surface: Smooth. Length: 60 mm. Diameter: 3.5 mm on average. Color: Yellow-Green Group 144A. Strength: Strong.

Flower bud development: Flower buds are borne single.

Flower bloom:

- *Fragrance*.—Light floral.
- *Duration*.—The blooms have a duration on the plant of approximately 21 days. Petals fall cleanly away from plant after flowers have fully matured.
- *Size*.—Flower diameter is 80 mm when open. Flower depth is 28 mm.
- *Flower shape*.—Rosette, very double flower with many slightly overlapping petals of different sizes.
- *Shape of flower, side view*.—The upper portion is flat. The lower portion is flat.

Petalage: Under normal conditions, flowers have about 85 petals.

General tonality of flower: Open flowers are Yellow-Orange Group 23B with intonations of Orange-Red Group 31A. As the flower matures color changes to Yellow-Orange Group 18A and other colors of Orange Group 29A.

Petal color:

- *Upon opening, outer petals*.—Upper surface: Orange Group 27A splashed with Red Group 47B. The basal zone is Yellow Group 5B with spot of Red Group 46C. Lower surface: Basal zone Yellow-Orange Group 16B. Splashes of Red Group 39B at the middle zone, and Red Group 49C at the marginal zone. Guard petals have intonations of Yellow-Green Group 145B.
- *Upon opening, inner petals*.—Upper surface: Yellow-Orange Group 16B splashed with Red Group 45D. Basal zone Yellow Group 12A. Lower surface: At the basal zone Yellow Group 8A with a spot of Red Group 43B. The middle and outer zone are Red Group 43B.
- *After opening, outer and inner petals*.—Upper surface: Yellow-Orange Group 16C splashed with Red Group 47B. Basal zone Yellow Group 12A marked with a spot of Red Group 45D. Lower surface: Yellow-Orange Group 18A splashed with Red Group 50B. Guard petals have other intonations of Yellow-Green Group 145B and Red Group 53C.

Petals:

- *Petal reflex*.—Strong, bilateral. Recurved inward.
- *Margin*.—Entire and uniform. No undulations.
- *Shape*.—Broad and elliptic. Apex shape: Rounded. Base shape: Rounded.
- *Size*.—About 40 mm (l)×43 mm (w).
- *Texture*.—Smooth.
- *Thickness*.—Average.

Petaloids:

- *Size*.—20 mm (l) by 15 mm (w).
- *Quantity*.—About 12.
- *Shape*.—Elliptical with an acute base and rounded apex.
- *Color*.—Undersurface, Yellow-Orange Group 16B with streaks of Red Group 47C. The upper surface is Yellow-Orange Group 16A splashed with Red Group 42B. The basal, point of attachment on the upper surface is Yellow Group 9A.

Reproductive flower parts:

- *Pollen*.—None observed.
- *Anthers*.—Size: About 1.5 mm in length. Color: Greyed-Yellow Group 160D. Quantity: About 20.
- *Filaments*.—Color: Yellow Group 10D. Length: 3 mm.
- *Pistils*.—Length: 7 mm. Quantity: 40 on average.
- *Stigmas*.—Color: Yellow-White Group 158B.
- *Styles*.—Color: Green-White Group 157B.
- *Location of stigmas*.—Superior in location relative to the length of the filaments and the height of the anthers.
- *Hips*.—None Observed.

PLANT

Plant growth: Upright. Plants are 40 to 50 cm in height, and 37 cm wide.

Stems:

- *Color of juvenile growth*.—Yellow-Green Group 144B.
- *Color of mature growth*.—Yellow-Green Group 144A.
- *Length*.—Canes are about 30 cm from the base of the plant to the flowering portion.
- *Diameter*.—About 5 mm.
- *Internodes*.—On mature canes about 30 to 44 mm between nodes.
- *Surface texture*.—Young wood: Smooth. Older wood: Smooth.

Long prickles: None observed.

Plant foliage:

*Compound leaf.*—115 mm (l)×80 mm (w).

*Quantity.*—3 leaves per 10 cm of stem on average.

*Leaf bearing angle to the stem.*—45 degrees.

*Color of juvenile foliage.*—Upper side: Yellow-Green Group 144A with intonations of Greyed-Purple Group 183B at margins. Lower side: Yellow-Green Group 148B shaded with Greyed-Purple Group 183A.

*Color of mature foliage.*—Upper side: Yellow-Green Group 146A. Lower side: Yellow-Green Group 147B.

Plant leaves and leaflets:

*Stipules.*—Size: 5 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 10 mm. Diameter: 2 mm. Upper surface color: Yellow-Green Group 144A and Greyed-Purple Group 185A. Lower surface color: Yellow-Green Group 144A.

*Rachis.*—Length: 43 mm. Upper surface color: Greyed-Purple Group 185A. Lower surface color: Yellow-Green Group 144A.

*Leaflet.*—Quantity: Normally 5 to 7 leaflets. Margins: Serrated. Size: Terminal leaflets are about 52 mm long, 35 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah110', substantially as illustrated and described herein, due to its abundant orange flowers, disease resistance, and extended period of bloom.

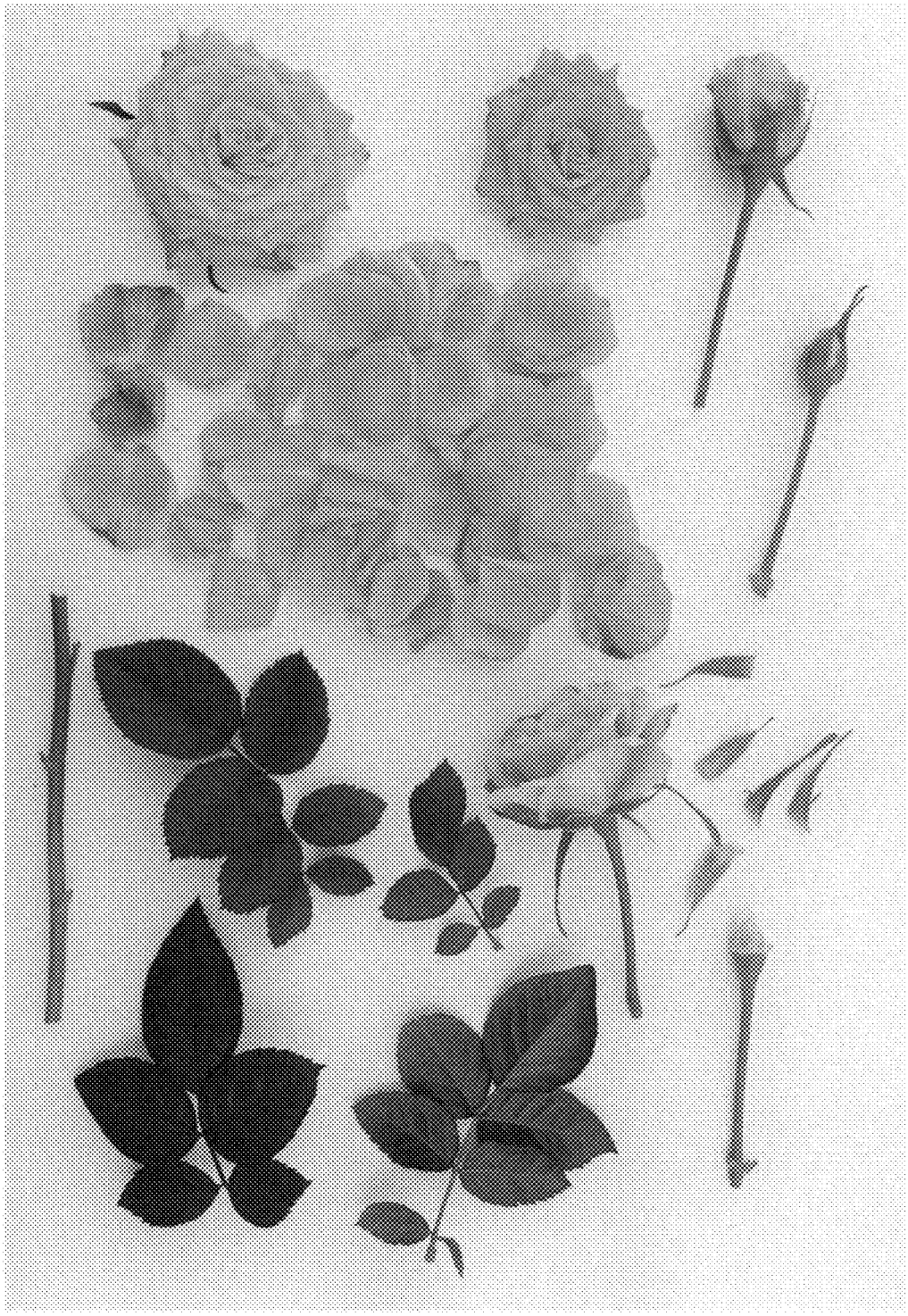

* * * * *